(12) United States Patent
Eckwright et al.

(10) Patent No.: US 10,814,128 B2
(45) Date of Patent: Oct. 27, 2020

(54) ELECTROPORATION CATHETER

(71) Applicant: COVIDIEN LP, Mansfield, MA (US)

(72) Inventors: Tyler J. Eckwright, Minneapolis, MN (US); Katherine A. Herdina, Minneapolis, MN (US); Carol L. Shaffer, Plymouth, MN (US)

(73) Assignee: COVIDIEN LP, Mansfield, MA (US)

( * ) Notice: Subject to any disclaimer, the term of this patent is extended or adjusted under 35 U.S.C. 154(b) by 103 days.

(21) Appl. No.: 15/787,894

(22) Filed: Oct. 19, 2017

(65) Prior Publication Data
US 2018/0140832 A1 May 24, 2018

Related U.S. Application Data

(60) Provisional application No. 62/424,784, filed on Nov. 21, 2016.

(51) Int. Cl.
*A61N 1/32* (2006.01)
*A61B 18/14* (2006.01)
(Continued)

(52) U.S. Cl.
CPC .......... *A61N 1/327* (2013.01); *A61B 18/1492* (2013.01); *A61B 18/1206* (2013.01);
(Continued)

(58) Field of Classification Search
CPC .......... A61B 18/1492; A61B 2018/147; A61B 2018/1492; A61B 2018/1497;
(Continued)

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 A 6/1995
CN 102970945 A 3/2013
(Continued)

OTHER PUBLICATIONS

U.S. Appl. No. 14/242,019, filed Apr. 1, 2014; inventor: Brannan.
(Continued)

*Primary Examiner* — Tiffany Legette

(57) ABSTRACT

A catheter includes first and second handles, first and second tubular members, and first and second electrodes. The first tubular member defines a channel therethrough and is coupled to and distally extends from the first handle. The second tubular member is coupled to and distally extends from the second handle. The second tubular member is slidably disposed within the channel of the first tubular member and defines a lumen therethrough. The first and second electrodes are configured to generate an electric field therebetween. The second handle is translatable relative to the first handle between a retracted position in which the second electrode is adjacent the first electrode and an extended position in which the second electrode is spaced apart from the first electrode.

16 Claims, 5 Drawing Sheets

(51) Int. Cl.
*A61B 18/12* (2006.01)
*A61B 17/00* (2006.01)
*A61B 18/00* (2006.01)

(52) U.S. Cl.
CPC .............. *A61B 2017/00703* (2013.01); *A61B 2018/00178* (2013.01); *A61B 2018/00613* (2013.01)

(58) Field of Classification Search
CPC .... A61B 2018/162; A61B 2018/00178; A61B 18/1206; A61B 34/20; A61B 2017/00703; A61B 2018/00613; A61B 2034/2051; A61N 1/325; A61N 1/327; A61N 1/30; A61N 1/303; A61N 1/306; A61N 1/044; A61N 1/0472; A61N 1/0432; A61N 1/0428; A61N 1/0424; A61N 1/0416; A61N 1/0412; A61N 1/326
See application file for complete search history.

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| 5,244,462 A | 9/1993 | Delahuerga et al. |
| D354,218 S | 1/1995 | Van de Peer |
| 5,569,289 A | 10/1996 | Yoon |
| D424,693 S | 5/2000 | Pruter |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |
| D487,039 S | 2/2004 | Webster et al. |
| D496,997 S | 10/2004 | Dycus et al. |
| D499,181 S | 11/2004 | Dycus et al. |
| 6,821,282 B2 | 11/2004 | Perry et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| 7,270,656 B2 | 9/2007 | Gowda et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 7,942,871 B2 | 5/2011 | Thapliyal et al. |
| 8,157,799 B2 | 4/2012 | Desinger et al. |
| 8,357,193 B2 | 1/2013 | Phan et al. |
| D681,810 S | 5/2013 | DeCarlo |
| 8,728,068 B2 | 5/2014 | Nye et al. |
| 2002/0016615 A1* | 2/2002 | Dev ................ A61N 1/325 607/2 |
| 2005/0245920 A1 | 11/2005 | Vitullo et al. |
| 2009/0118727 A1 | 5/2009 | Pearson et al. |
| 2009/0163861 A1* | 6/2009 | Carlyon .............. A61M 5/3273 604/110 |
| 2009/0299352 A1 | 12/2009 | Zerfas et al. |
| 2010/0280495 A1 | 11/2010 | Paul et al. |
| 2012/0238806 A1 | 9/2012 | Mangiardi et al. |
| 2012/0289772 A1 | 11/2012 | O'Connell et al. |
| 2012/0310230 A1* | 12/2012 | Willis .................. A61N 1/327 606/33 |
| 2013/0023729 A1 | 1/2013 | Vazales et al. |
| 2013/0030249 A1 | 1/2013 | Vazales et al. |
| 2013/0046297 A1 | 2/2013 | Lingeman et al. |
| 2013/0060240 A1 | 3/2013 | Scheller et al. |
| 2013/0123757 A1 | 5/2013 | Crisostomo et al. |
| 2013/0123898 A1 | 5/2013 | Tung et al. |
| 2013/0123912 A1 | 5/2013 | Tung et al. |
| 2013/0144276 A1 | 6/2013 | Crisostomo et al. |
| 2013/0158655 A1 | 6/2013 | Sutton et al. |
| 2013/0231557 A1 | 9/2013 | Li et al. |
| 2014/0046174 A1 | 2/2014 | Ladtkow et al. |
| 2014/0081308 A1 | 3/2014 | Wondka et al. |
| 2014/0114125 A1 | 4/2014 | Scopton et al. |
| 2014/0276033 A1 | 9/2014 | Brannan et al. |
| 2015/0073407 A1* | 3/2015 | Dickhans ........... A61B 18/1815 606/41 |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| EP | 1929956 A2 | 6/2008 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |

(56) References Cited

FOREIGN PATENT DOCUMENTS

| | | |
|---|---|---|
| FR | 2 862 813 A1 | 5/2005 |
| FR | 2 864 439 A1 | 7/2005 |
| JP | 56-161636 | 12/1981 |
| JP | 59-58933 | 4/1984 |
| JP | 5-5106 | 1/1993 |
| JP | 5-08933 | 2/1993 |
| JP | 05-40112 | 2/1993 |
| JP | 06343644 A | 12/1994 |
| JP | 07265328 A | 10/1995 |
| JP | H08-56955 | 5/1996 |
| JP | 08252263 A | 10/1996 |
| JP | 910223 | 1/1997 |
| JP | 09000492 A | 1/1997 |
| JP | 9117456 | 5/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2002253569 A | 9/2002 |
| JP | 2004097537 A | 4/2004 |
| JP | 2005522274 A | 7/2005 |
| JP | 2006305361 A | 11/2006 |
| JP | 2008142467 A | 6/2008 |
| KR | 20070093068 A | 9/2007 |
| KR | 20100014406 A | 2/2010 |
| KR | 20120055063 A | 5/2012 |
| SU | 166452 | 1/1965 |
| SU | 401367 A1 | 10/1973 |
| SU | 727201 A2 | 4/1980 |
| WO | 00/36985 A2 | 6/2000 |
| WO | 2010/035831 A1 | 4/2010 |
| WO | 2011062035 A1 | 5/2011 |
| WO | 2016033090 A1 | 3/2016 |

OTHER PUBLICATIONS

U.S. Appl. No. 14/242,048, filed Apr. 1, 2014; inventor: Prakash.
U.S. Appl. No. 14/281,264, filed May 19, 2014; inventor: Prakash.
U.S. Appl. No. 14/281,344, filed May 19, 2014; inventor: Shiu.
U.S. Appl. No. 14/300,824, filed Jun. 10, 2014; inventor: Behnke.
U.S. Appl. No. 14/300,871, filed Jun. 10, 2014; inventor: Bonn.
U.S. Appl. No. 14/306,865, filed Jun. 17, 2014; inventor: Brannan.
U.S. Appl. No. 62/020,240, filed Jul. 2, 2014, inventor Andrew Brown.
International Search Report dated Dec. 11, 2014 issued in PCT/US2014/054511.
Luo Xiongbiao et al., "Beyond Current Guided Bronchoscopy: A Robust and Real-Time Bronchoscopic Ultrasound Navigation System", In: "Lecture Notes in Computer Science (LNCS): Medical Image Computing and Computer-Assisted Intervention—MCCAI 2013", Sep. 22, 2013, vol. 8149, pp. 388-395, XP047041936.
Yehuda Schwarz: "Electromagnetic Navigation", Clinics in Chest Medicine, vol. 31, No. 1, Mar. 1, 2010, pp. 65-73, XP055131118.
F.J.F. Herth: "Bronchoscopic Techniques in Diagnosis and Staging of Lung Cancer", Breathe, vol. 7, No. 4, Jun. 1, 2011, pp. 324-337, XP055358488.
William Krimsky et al: "Bronchoscopy and the Peripheral Nodule in the Age of Lung Cancer Screening and Targeting Therapies", Current Respiratory Care Reports, vol. 1, No. 1, Jan. 25, 2012, pp. 67-71, XP055358485.
European Search Report dated Apr. 11, 2017, issued in EP Application No. 14842294.
Japanese Office Action dated Jun. 20, 2017, issued in JP Application No. 2016540341.
Supplemental European Search Report dated Jun. 26, 2017, issued in EP Application No. 14843010.
Japan Electronics and Information Technology Industries Association, Kaitei Iyou Choonpa Kiki Handobuku, Japan, Corona, Jan. 20, 1997, p. 15, p. 35. (A part or the whole of the non-patent literature indicated above may not be forwarded due to restrictions arising from law or contract.)
Chinese Office Action dated Aug. 18, 2017, issued in CN Application No. 201480057462.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lydon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

(56) References Cited

OTHER PUBLICATIONS

Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'L Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Stagegaard, N., Petersen H-H., Chen X., Svendsen J.H., "Indication of the Radiofrequency Induced Lesion Size by Pre-ablation Measurements" Europace (2005) 7, 525-534.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993; Roger A. Stern.
U.S. Appl. No. 08/483,742, filed Jun. 7, 1995; Roger A. Stern.
U.S. Appl. No. 14/011,414, filed Aug. 27, 2013; inventor: Ohri.
U.S. Appl. No. 14/011,438, filed Aug. 27, 2013; inventor: Ohri.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas MedicalCenter,Chartotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.

(56) References Cited

OTHER PUBLICATIONS

Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radio!, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

\* cited by examiner

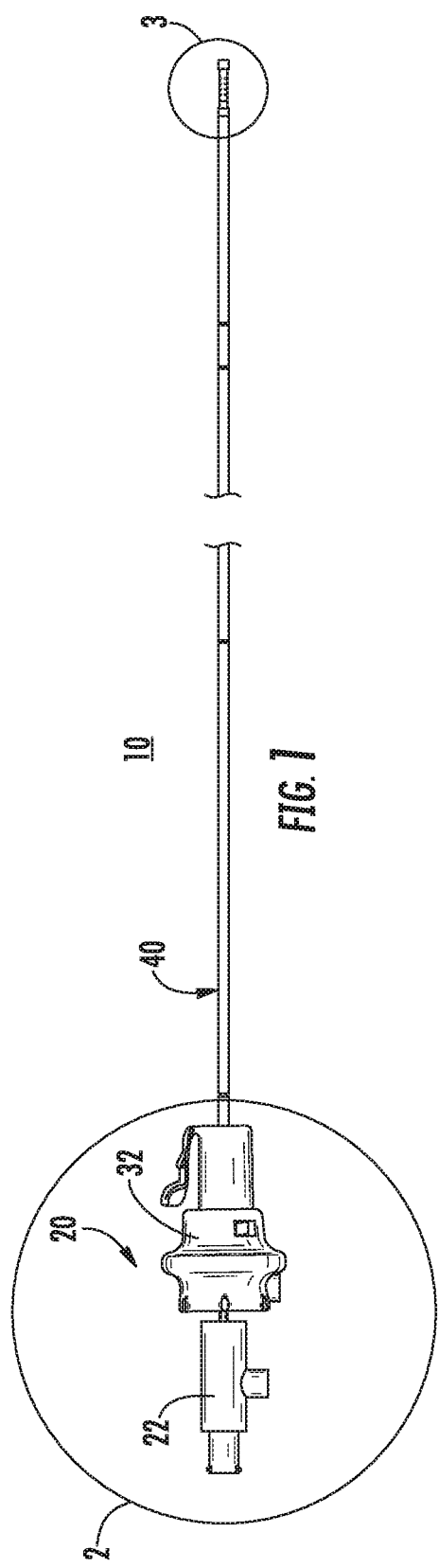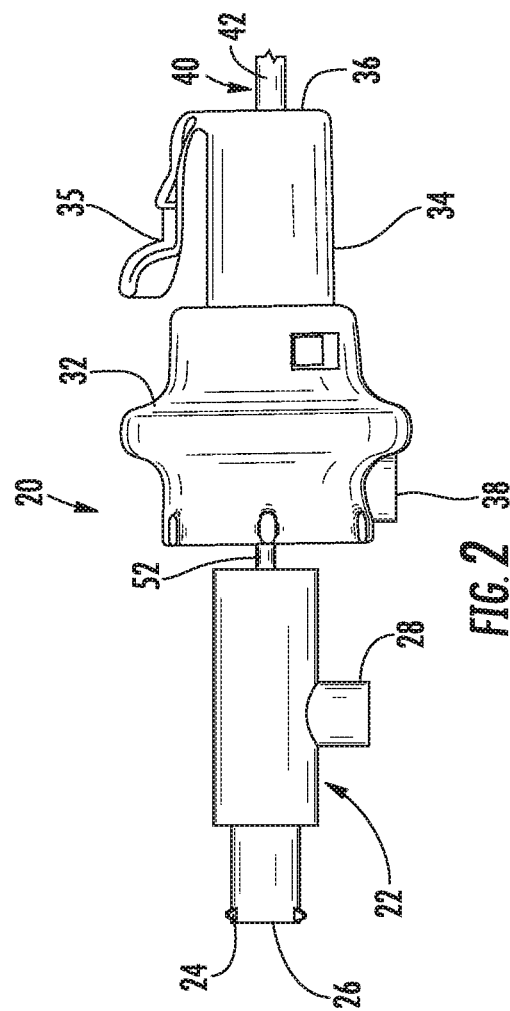

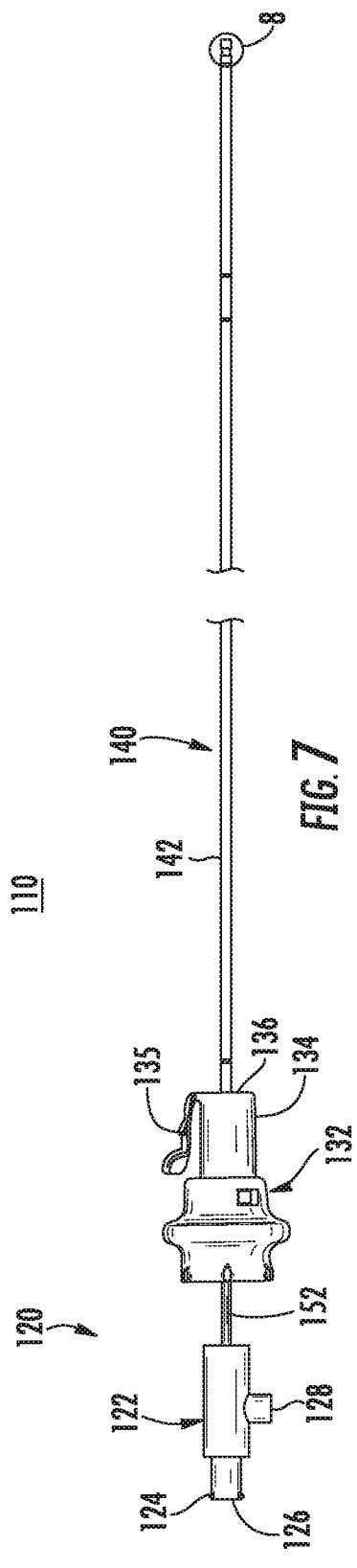
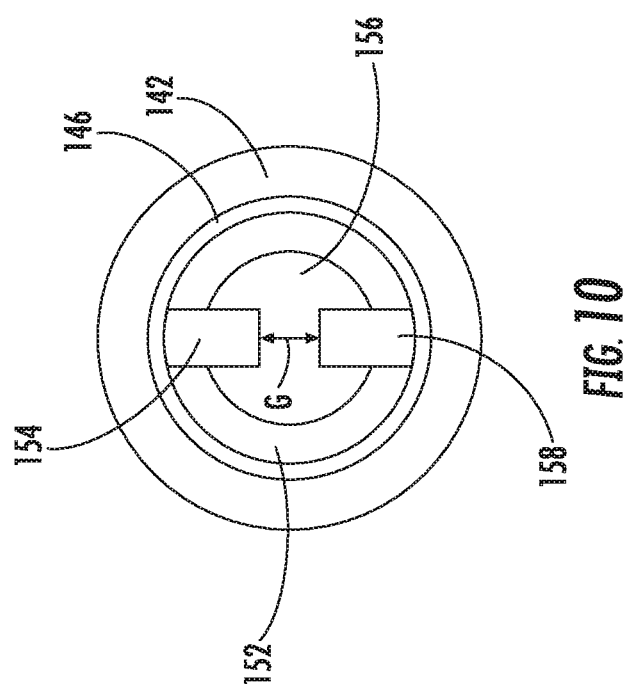
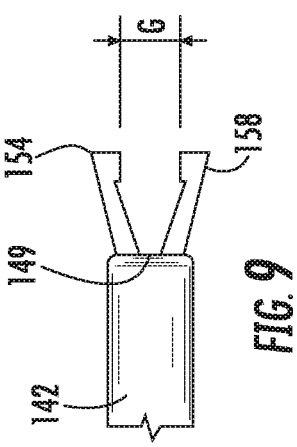
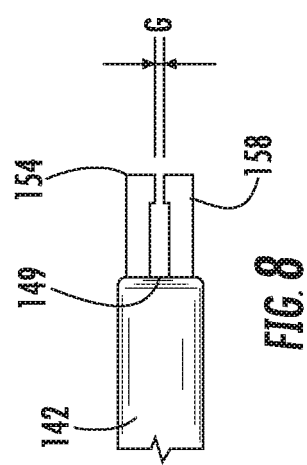

ELECTROPORATION CATHETER

CROSS REFERENCE TO RELATED APPLICATION

The present application claims the benefit of and priority to U.S. Provisional Application Ser. No. 62/424,784, filed on Nov. 21, 2016 the entire contents of which are incorporated herein by reference.

BACKGROUND

1. Technical Field

The present disclosure relates to catheters and, more specifically, to catheters for creating an electrical field to aid in delivering therapies to cells.

2. Discussion of Related Art

Current research is indicating that genomic therapies are may be effective treatment for lung and lymphatic cancers. For genomic therapies to be effective, the genomic therapies must pass through cell membranes or walls to enter into cells. The genomic therapies can be large such that pores in the cell membranes must be opened to allow the genomic therapies to enter into the cells.

One method to open pores in the cell membranes is electroporation which uses an electric field to open pores in cell membranes to allow genomic therapies to enter cells. To be effective, the electrical field must be precisely generated at the cells to be treated. However, current technology is limited in how precisely the electrical field can be positioned and generated.

Therefore, there is a continuing need for devices and methods for generating an electrical field at and/or adjacent targeted cells to allow for genomic therapies to enter into targeted cells.

SUMMARY

In an aspect of the present disclosure, a catheter includes first and second handles, first and second tubular members, and first and second electrodes. The first tubular member defines a channel therethrough and is coupled to and distally extends from the first handle. The second tubular member is coupled to and distally extends from the second handle. The second tubular member is slidably disposed within the channel of the first tubular member and defines a lumen therethrough. The first and second electrodes are configured to generate an electric field therebetween. The second handle is translatable relative to the first handle between a retracted position in which the second electrode is adjacent the first electrode and an extended position in which the second electrode is spaced apart from the first electrode.

In aspects, the first and second tubular members are coaxial with one another. The second handle may define an opening that is in communication with the lumen of the second tubular member. The second handle may include a connector in communication with the lumen of the second tubular member. The first and second electrodes may be configured to generate an electric field therebetween during delivery of a molecule to cells adjacent a distal portion of the second tubular member via the lumen. The first handle may include a tab that is configured to engage a port to secure the second handle to the port.

In some aspects, the first electrode is positioned on a distal portion of the first tubular member and the second electrode is positioned on a distal portion of the second tubular member. The first handle may include a first electrical connector in communication with the first electrode and the second handle may include a second electrical connector in communication with the second electrode. The first and second electrodes may be configured to connect to a source of electrosurgical energy.

In certain aspects, the first and second electrodes are positioned on a distal portion of the second electrode and define a gap therebetween. In the retracted position, the gap may have a first dimension and in the extended position the gap may have a second dimension that is larger than the first dimension. The first and second dimensions may be defined transverse to a central longitudinal axis of the distal portion of the second tubular member. The first and second electrodes may be pivotal relative to one another.

In another aspect of the present disclosure, a surgical system includes an electromagnetic navigation system, an electrosurgical energy source, and a catheter. The catheter includes first and second handles, first and second tubular members, and first and second electrodes. The first tubular member is coupled to and distally extends from the first handle. The first tubular member defines a channel therethrough. The second tubular member is coupled to and distally extends from the second handle. The second tubular member is slidably disposed within the channel of the first tubular member and defines a lumen therethrough. The first electrode is in electrical communication with the electrosurgical energy source. The second electrode in electrical communication with the electrosurgical energy source. The first and second electrodes are configured to generate an electrical field therebetween. The second handle is transitionable relative to the first handle between a retracted position in which the second electrode is adjacent the first electrode and an extended position in which the second electrode is spaced apart from the first electrode.

In aspects, the electromagnetic navigation system includes a tracking system and a sensor. The tracking system may be configured to detect the position of the sensor within a patient. The sensor may be disposed on the second tubular member.

In another aspect of the present disclosure, a method of delivering molecules to targeted cells includes positioning a catheter adjacent targeted cells such that a distal portion of a first tubular member of the catheter is adjacent the targeted cells, extending a second tubular member from the distal portion of the first tubular member, generating an electric field between first and second electrodes of the catheter to effect electroporation of the targeted cells, and delivering a molecule through a lumen of the second tubular member to the targeted cells.

In aspects, delivering the molecule through the lumen of the lumen of the second tubular member occurs during generating the electric field between the first and second electrodes. Extending the second tubular member from the distal portion of the first tubular member may include distally translating the second electrode, which is disposed on a distal portion of the second tubular member, distally away from the first electrode, which is disposed on the distal portion of the first tubular member.

In some aspects, the extending the second tubular member from the distal portion of the first tubular member includes pivoting the first and second electrodes away from tone another in a direction transverse to a longitudinal axis of a distal end portion of the second tubular member. Positioning the catheter adjacent the targeted cells may include utilizing a tracking system to navigate a patient's airways.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 1 is a side view of an exemplary catheter provided in accordance with the present disclosure;

FIG. 2 is an enlarged view of the indicated area of detail of FIG. 1 illustrating a handle assembly of the catheter in an extended configuration;

FIG. 7 is a side view of another exemplary catheter provided in accordance with the present disclosure;

FIG. 8 is an enlarged view of the indicated area of detail of FIG. 7 illustrating a distal portion of the catheter of FIG. 7 in a first extended configuration;

FIG. 9 is a side view of the distal portion of the catheter of FIG. 8 in a second extended configuration;

FIG. 10 is an end view of the distal portion of the catheter of FIG. 8; and

DETAILED DESCRIPTION

Figure 3:
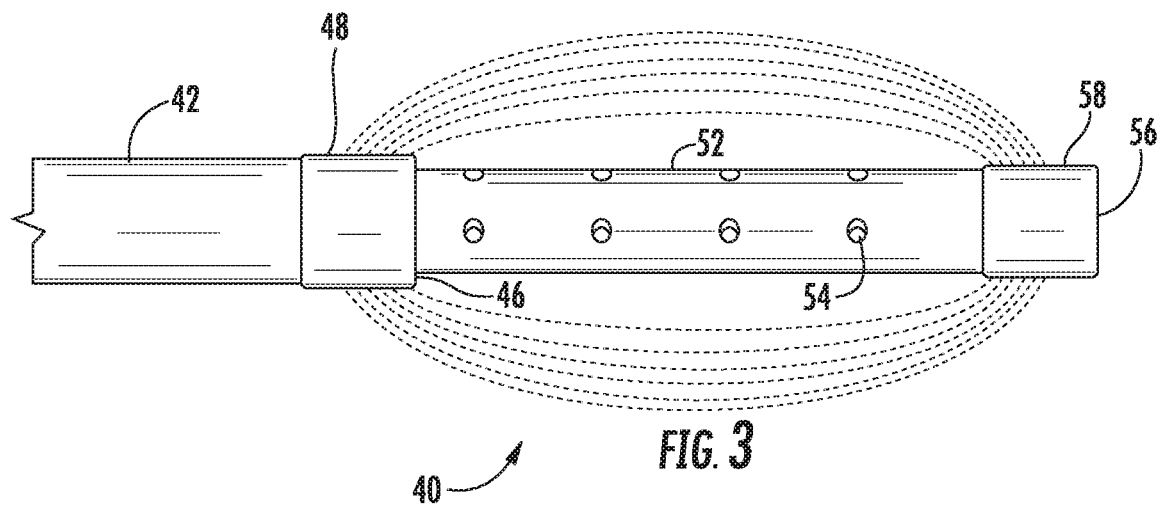
FIG. 3 is an enlarged view of the indicated area of detail of FIG. 1 illustrating a tubular assembly of the catheter in the extended configuration.

This disclosure relates generally to catheters and methods for creating an electrical field adjacent targeted cells to allow molecules (e.g., genomic therapies) to pass through cell membranes or walls of target cells. The electrical fields may be configured to open pores in the cell walls of the target cells through electroporation to allow molecules to pass through the cell walls to enter the target cells. The catheter includes first and second electrodes that are positionable relative to one another such that an electrical field generated between the first and second electrodes opens pores in cell walls of target cells to permit molecules to enter the target cells. In addition, the catheter may include a lumen defined from a handle to a distal portion positioned adjacent target cells such that a molecule can be delivered to the target cells through the catheter as the electrical field is generated between the first and second electrodes.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, an exemplary catheter 10 provided in accordance with the present disclosure includes a handle assembly 20 and a tubular assembly 40. The handle assembly 20 is configured to be received in an access device or port (e.g., bronchoscope 390 (FIG. 10)) as detailed below.

With additional reference to FIG. 2, the handle assembly 20 includes a proximal handle 22 and a distal handle 32. The proximal handle 22 includes a proximally extending connector 24 that defines an opening 26 therethrough. The connector 24 may be a luer connector or any other suitable connector. The proximal handle 22 is mechanically coupled to an inner tubular member 52 of the tubular assembly 40 such that the inner tubular member 52 translates and/or rotates with the proximal handle 22 as described in detail below. The opening 26 is in communication with a lumen 56 (FIG. 4) defined by the inner tubular member 52. The proximal handle 22 also includes an electrical connector 28 for connecting to an external energy source (e.g., generator 490 (FIG. 11)) to receive a first energy potential as detailed below.

The distal handle 32 is coaxial with the proximal handle 22 and defines a passage 36 that allows the inner tubular member 52 to pass through the distal handle 32. The distal handle 32 includes a neck 34 that is configured to be received in an access device or port as detailed below. The neck 34 may include a tab 35 that is configured to engage the access device or port to longitudinally and/or rotatably secure the distal handle 32 to the access device or port. The distal handle 32 is coupled to an outer tubular member 42 of the tubular assembly 40 such that the outer tubular member 42 translates and/or rotates with the distal handle 32 as described in detail below. The distal handle 32 may include an electrical connector 38 for connecting to an external energy source (e.g., generator 490 (FIG. 11)) to receive a second energy potential different from the first energy potential as detailed below.

Referring now to FIG. 3, the tubular assembly 40 extends distally from the handle assembly 20 and includes the outer tubular member 42 and the inner tubular member 52. The outer tubular member 42 includes a first electrode 48 that is in electrical communication with the electrical connector 38 (FIG. 2) of the handle assembly 20. The outer tubular member 42 slidably receives the inner tubular member 52 within the channel 46 such that a distal portion of the inner tubular member 52 is extendable beyond the first electrode 48.

Figure 4:
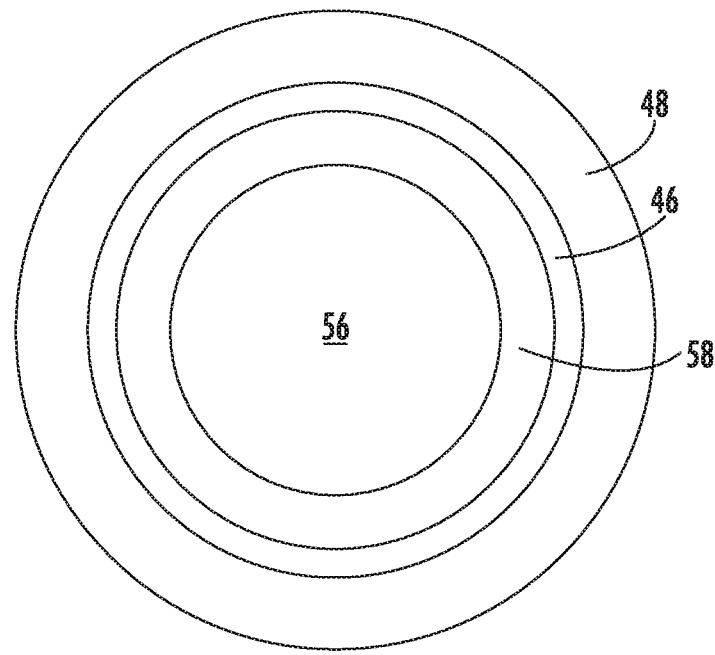
FIG. 4 is a distal end view of the tubular assembly of FIG. 3.

With additional reference to FIG. 4, the inner tubular member 52 (FIG. 3) defines a lumen 56 that is in communication with the opening 26 (FIG. 2) of the handle assembly 20 such that molecules can be delivered or a vacuum applied through the lumen 56 from the opening 26 without the need for an instrument or device to be passed through the opening 26. For example, a container (not shown) may be coupled to the connector 24 such that molecules from within the container flow through the lumen 56. It is also contemplated that an instrument or device or portion thereof (e.g., syringe 500 (FIG. 11)) can be passed entirely the tubular assembly 40.

The distal portion of the inner tubular member 52 may include holes 54 longitudinally and radially spaced apart from one another. The holes 54 can allow for molecules to flow from within the lumen 56 to tissue or cells surrounding the distal portion of the inner tubular member 52.

Referring briefly back to FIGS. 2 and 3, the catheter 10 has a first or extended configuration in which the second electrode 58 extends distally from the first electrode 48 such that a distal portion of the inner tubular member 52 is exposed between the first and second electrodes 48, 58. The position of the second electrode 58 relative to the first electrode 48 is affected by the position of the proximal handle portion 22 relative to the distal handle 32. It is contemplated that a surface of the inner tubular member 52 between the proximal handle 22 and the distal handle 32 may include markings indicating the distance that the second electrode 58 is extended from the first electrode 48. It is contemplated that the distance between the first and second electrodes 48, 58 affects the electric field generated by the catheter 10 as detailed below.

To generate the electric field between the first and second electrodes 48, 58, energy is supplied to the first and second electrodes 48, 58. This energy may be pulsed and is calibrated for the characteristics of the target cells such that the electric field generated between first and second electrodes 48, 58 creates or opens pores in the walls of the target cells such that molecules can enter the target cells. For a detailed description of electroporation of targeted cells reference can be made to U.S. Pat. Nos. 5,543,440 and 5,993,434.

Figure 5:
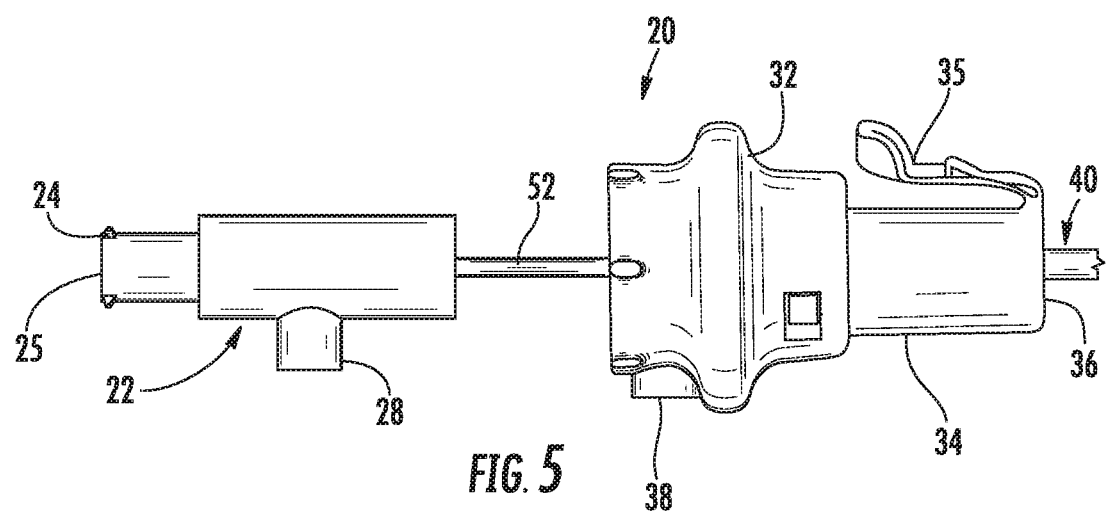
FIG. 5 is a side view of the handle assembly of FIG. 2 in a retracted position.
Figure 6:
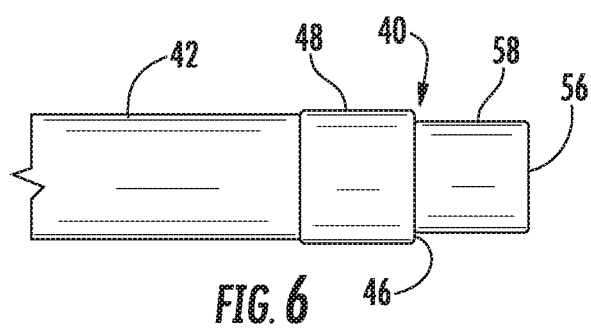
FIG. 6 is a side view of the tubular assembly shown in FIG. 3 of the catheter in the retracted position.

With reference to FIGS. 5 and 6, the catheter 10 has a second or retracted configuration in which the second electrode 58 is positioned substantially within the channel 46 of the outer tubular member 42. As shown in FIG. 5, the proximal handle 22 is moved proximally from the extended configuration (FIG. 2) to retract or withdraw the second electrode 58.

Referring now to FIGS. 7-9, another catheter 110 is provided in accordance with the present disclosure and includes a handle assembly 120 and a tubular assembly 40. Several elements of catheter 110 are similar to elements of catheter 10 detailed above and are represented with similar labels with a "1" preceding the previous label and will not be detailed herein below except for distinguishing catheter 110 from catheter 10.

The handle assembly 110 includes a proximal handle 122 and a distal handle 132 that are translatable along a common longitudinal axis relative to one another. The proximal handle 122 includes an electrical connector 128 that is configured to connect to an external energy source (e.g., generator 490 (FIG. 11)) as detailed below. The electrical connector 128 can receive a first energy potential and a second energy potential. An inner tubular member 152 of the tubular assembly 140 is mechanically coupled to the proximal handle 122.

With particular reference to FIG. 8, a distal portion of the inner tubular member 152 is extendable from a distal end 149 of an outer tubular member 142. The distal portion of the inner tubular member 152 includes a first electrode 154 and a second electrode 158 that define a gap "G" therebetween. The extent the first and second electrodes 154, 158 extend from the distal end 149 of the outer tubular member 142 and/or the gap "G" therebetween is affected by position of the proximal handle 122 relative to the distal handle 132.

The proximal and distal handles 122, 132 have a retracted configuration (not explicitly shown) in which the first and second electrodes 154, 158 are disposed within the distal end 149 of the outer tubular member 142. The proximal and distal handles 122, 132 have a first extended configuration in which the first and second electrodes 154, 158 extend from the distal end 149 of the outer tubular member 142 in which the gap "G" between the first and second electrodes 154, 158 has a first dimension as shown in FIG. 8. In addition, the proximal and distal handles 122, 132 may have a second extended configuration, such that the proximal handle 122 is closer to the distal handle 132 than in the first extended configuration, in which the first and second electrodes 154, 158, extend from the distal end 149 of the outer tubular member 142 and the gap "G" has a second dimension larger than the first dimension as shown in FIG. 9. It is contemplated that the first and second electrodes 154, 158 can be used to grasp tissue therebetween. In such embodiments, the first and second electrodes 154, 158 can be used to electroporate cells of the grasped tissue.

With additional reference to FIG. 10, the inner tubular member 152 defines a lumen 156 that is in communication with an opening 126 in the proximal handle 122 to allow an instrument and/or molecules to be inserted through the opening 126 and to exit the lumen 156 adjacent the first and second electrodes 154, 158.

Figure 11:
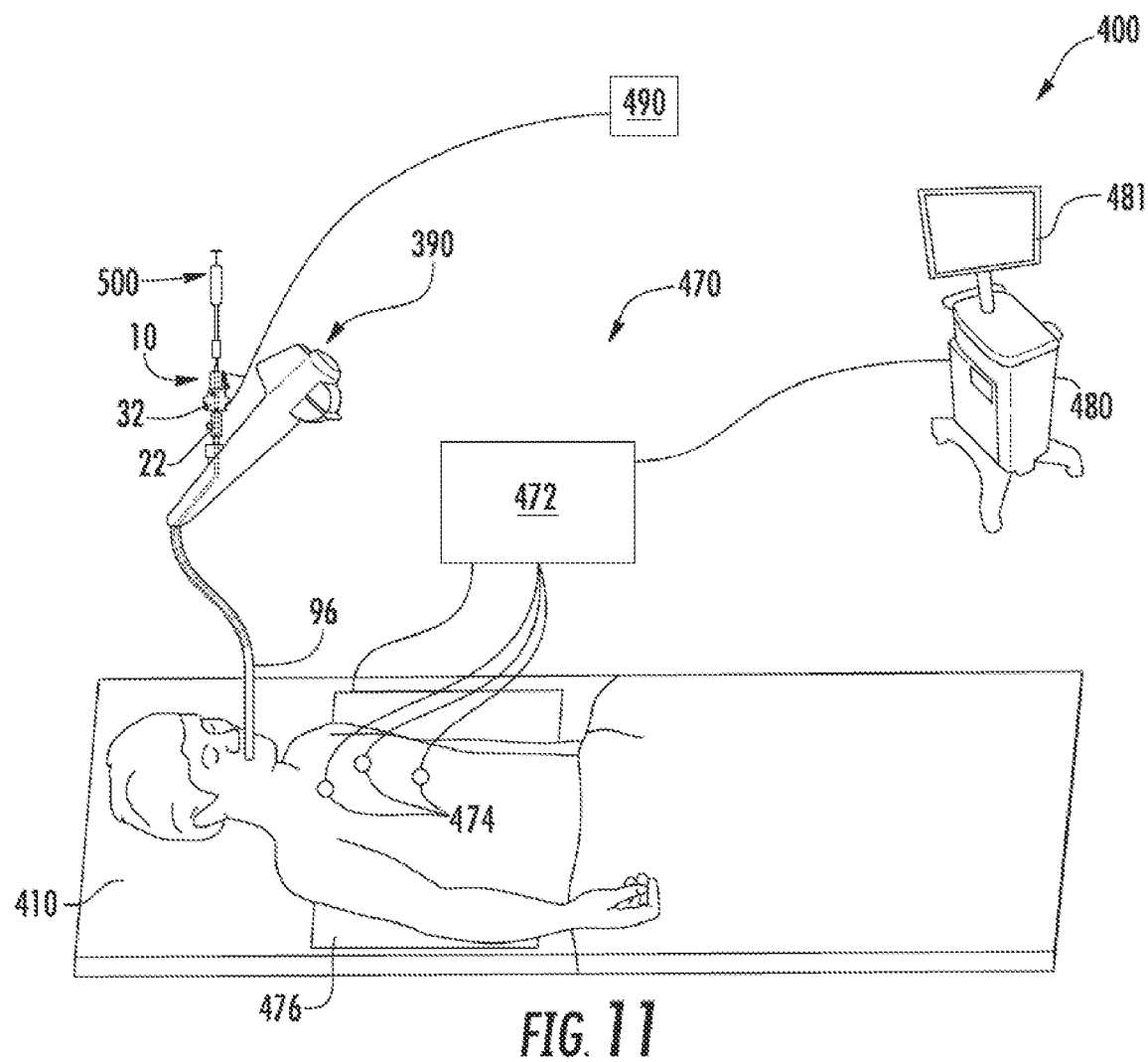
FIG. 11 is a perspective view of an exemplary surgical system including the catheter of FIG. 1.

With reference to FIG. 11, an electromagnetic navigation (EMN) system 400 is provided in accordance with the present disclosure to position a distal portion of a catheter (e.g., catheter 10 or 110) adjacent target cells. FIG. 11 also depicts the catheter 10 for use with the EMN system 400; however, it is contemplated that other catheters (e.g., catheter 110) may also be used with EMN system 400. One such EMN system is the ELECTROMAGNETIC NAVIGATION BRONCHOSCOPY® system currently sold by Covidien LP. Among other tasks that may be performed using the EMN system 400 are planning a pathway to target cells, navigating a catheter guide assembly to the target cells, deploying an instrument adjacent or into the target cells to treat or capture the target cells, digitally marking the location of the target cells in a data file related to the planned pathway, and placing one or more echogenic markers at or around the target cells.

The EMN system 400 generally includes an operating table 410 configured to support a patient; a bronchoscope 390 configured for insertion through the patient's mouth and/or nose into the patient's airways; a tracking system 470 including a tracking module 472, a plurality of reference sensors 474, and an electromagnetic field generator 476; and a workstation 480 including software and/or hardware used to facilitate pathway planning, identification of target cells, navigation to target cells, and digitally marking the biopsy location.

The EMN system 400 is used to position a tubular member 96 of the bronchoscope adjacent target cells. It is contemplated that an extended working channel (EWC) (not explicitly shown) may be passed through the tubular member 96 to be positioned adjacent target cells. The EMN system 400 may include a locatable guide (LG) catheter (not shown) to position the EWC adjacent target cells. An example of a similar catheter guide assembly is currently marketed and sold by Covidien LP under the name EDGE™ Procedure Kits. For a more detailed description of the use of the catheter guide assembly reference is made to commonly-owned U.S. Patent Publication 2016/0000302, the entire contents of which are hereby incorporated by reference. Alternatively, the first and/or second electrode 48, 58 of the catheter 10 can include a sensor visible to the EMN system 400 that can be used to position the tubular member 96 adjacent target cells.

With the tubular member 96 positioned adjacent target cells, the catheter 10 is passed through the tubular member 96 until the outer tubular member 42 (FIG. 3) extends from the tubular member 96. Fluoroscopy can be used to confirm the location of the outer tubular member 42. With the outer tubular member 42 extended from the tubular member 96, a syringe 500 filled with a molecule (e.g., a genomic therapy, etc.) is connected to the connector 24 (FIG. 2). The syringe 500 may be configured to expel molecules into the opening 26 of the proximal handle 22 such that the molecules flow through the inner tubular member 52 and exits adjacent the second electrode 58. For example, the molecules may flow from the openings 54 in the distal portion of the inner tubular member 52. Alternatively, the syringe 500 may extend such that a distal portion of the syringe 500 is positioned adjacent the second electrode 58 (FIG. 3). It is contemplated that a distal portion of the syringe 500 may be positioned within the distal portion of the inner tubular member 52 or extend from the distal end of the inner tubular member 52.

A generator 490 is connected to the catheter 10 via electrical connectors 28, 38 (FIG. 2). With the generator 490 and the syringe 500 connected to the catheter 10 the proximal handle 22 is moved towards the distal handle 32 to extend the inner tubular member 52 such that the second electrode 58 is spaced apart from the first electrode 48. The position of the first and second electrodes 48, 58 may be verified using the EMN system as detailed above.

With the first and second electrodes 48, 58 positioned, the generator 490 is activated to generate an electric field between the first and second electrodes 48, 58. The electric field is configured to create electroporation in target cells such that molecules can pass through cell walls of the target cells. With the electric field active, the syringe 500 is extended to expel molecules from the inner tubular member 52 into the target cells. When the molecules are expelled, and after sufficient time to allow for the cells with the increased porosity size to take up the molecules, the generator 490 is deactivated and the catheter 10 is withdrawn or repositioned adjacent subsequent target cells. Upon deactivation the pores created in the cell walls is repaired by the cells. As the cell walls are repaired the molecules can be effectively trapped within the cell expediting treatment.

It is contemplated that the generator 490 can control the wave shape of the applied energy as well as the intensity and timing to allow for a series of pulses to be delivered to the target cells by the first and second electrodes. In addition, the generator 490 can receive electrocardiogram input, supplied through an EKG interface or another method, to synchronize energy delivery with the electrocardiogram input. For example, the energy deliver may be synchronized with an R wave signal to ensure that energy delivery is terminated during cardio repolarization/relative refractory or T-wave to reduce the potential for inducing ventricular fibrillation. In addition, intensity of the electric field generated during electroporation can reach several hundred volts per centimeter. The individual pulses of energy delivery may measure from microseconds to milliseconds in length, keeping the total application time under about one second. The shaping of these pulses may be square or sinusoidal; however, saw tooth waves have been contemplated.

While the use of the catheter 10 is detailed herein for use in the airway of a patient, it is contemplated that the catheter 10 may be used in a variety of surgical procedures utilizing elongated surgical instruments with extended working channels. For example, the catheter 10 may be used during various endovascular procedures such as cardiac interventions, general vascular interventional procedures, cerebral interventions, etc. These procedures may include, but are not limited to, balloon dilations, stent placements, percutaneous valve replacement, and percutaneous valve repair, pacing lead placement, cardiac ablation procedures, and electrical mapping procedures.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A catheter comprising:
   a first handle having a distal portion that is configured to be received within an access port of a bronchoscope to couple the first handle to the bronchoscope;
   a second handle;
   a first tubular member coupled to and distally extending from the first handle, the first tubular member defining a channel therethrough;
   a second tubular member coupled to and distally extending from the second handle, the second tubular member slidably disposed within the channel of the first tubular member and defining a lumen therethrough in fluid communication with a plurality of openings defined through a distal portion of the second tubular member;
   a first electrode; and
   a second electrode, the first and second electrodes configured to generate an electric field therebetween,
   wherein the second handle is translatable relative to the first handle between a retracted position in which the second electrode is adjacent the first electrode and the distal portion of the second tubular member is disposed within the first tubular member, and an extended position in which the second electrode is spaced apart from the first electrode and the distal portion of the second tubular member extends distally beyond the first electrode to expose the plurality of openings to tissue in proximity to the first and second electrodes for delivering therapeutic molecules to the tissue via the plurality of openings while the first and second electrodes are generating the electric field to treat the tissue.

2. The catheter according to claim 1, wherein the first and second tubular members are coaxial with one another.

3. The catheter according to claim 1, wherein the second handle defines an opening in communication with the lumen of the second tubular member.

4. The catheter according to claim 1, wherein the second handle includes a connector in communication with the lumen of the second tubular member.

5. The catheter according to claim 1, wherein the distal portion of the first handle includes a tab configured to engage the bronchoscope when the distal portion of the first handle is received within the access port to secure the first handle to the bronchoscope.

6. The catheter according to claim 1, wherein the second handle is disposed separate from the first handle when the second handle is in the extended position.

7. The catheter according to claim 1, wherein the first handle includes a distal neck portion having a reduced diameter relative to a proximal portion of the first handle, the distal neck portion configured to be received within the access port of the bronchoscope to couple the first handle to the bronchoscope.

8. The catheter according to claim 1, wherein the first electrode is positioned on a distal portion of the first tubular member and the second electrode is positioned on the distal portion of the second tubular member.

9. The catheter according to claim 8, wherein the first handle includes a first electrical connector in communication with the first electrode and the second handle includes a second electrical connector in communication with the second electrode, the first and second electrodes configured to connect to a source of electrosurgical energy.

10. A surgical system comprising:
an electromagnetic navigation system;
an electrosurgical energy source;
a bronchoscope having an access port; and
a catheter including:
a first handle having a distal portion that is configured to be received within the access port of the bronchoscope to couple the first handle to the bronchoscope;
a second handle;
a first tubular member coupled to and distally extending from the first handle, the first tubular member defining a channel therethrough;
a second tubular member coupled to and distally extending from the second handle, the second tubular member slidably disposed within the channel of the first tubular member and defining a lumen therethrough in fluid communication with a plurality of openings defined through a distal portion of the second tubular member;
a first electrode in electrical communication with the electrosurgical energy source; and
a second electrode in electrical communication with the electrosurgical energy source, the first and second electrodes configured to generate an electric field therebetween,
wherein the second handle is translatable relative to the first handle between a retracted position in which the second electrode is adjacent the first electrode and the distal portion of the second tubular member is disposed within the first tubular member, and an extended position in which the second electrode is spaced apart from the first electrode and the distal portion of the second tubular member extends distally beyond the first electrode to expose the plurality of openings to tissue in proximity to the first and second electrodes for delivering therapeutic molecules to the tissue via the plurality of openings while the first and second electrodes are generating the electric field to treat the tissue.

11. The system according to claim 10, wherein the electromagnetic navigation system includes a tracking system and a sensor, wherein the tracking system is configured to detect a position of the sensor within a patient.

12. The surgical system according to claim 10, wherein the second handle is disposed separate from the first handle when the second handle is in the extended position.

13. The surgical system according to claim 10, wherein the first handle includes a distal neck portion having a reduced diameter relative to a proximal portion of the first handle, the distal neck portion configured to be received within the access port of the bronchoscope to couple the first handle to the bronchoscope.

14. A catheter for use with a bronchoscope, comprising:
a first tubular member defining a channel therethrough and having a handle coupled to a proximal portion thereof that is configured to be received within an access port of a bronchoscope to couple the handle of the first tubular member to the bronchoscope;
a second tubular member slidably disposed within the channel of the first tubular member and defining a lumen therethrough, a distal portion of the second tubular member defining a plurality of openings in fluid communication with the lumen;
a first electrode disposed at a distal end portion of the first tubular member; and
a second electrode disposed on the distal portion of the second tubular member distal to the plurality openings, the first and second electrodes configured to generate an electric field therebetween, the second tubular member movable within the first tubular member to move the second electrode longitudinally relative to the first electrode and move the distal portion of the second tubular member between a first position wherein the plurality of openings are disposed within the first tubular member and a second position wherein the plurality of openings are disposed distal to the first electrode and in fluid communication with tissue disposed in proximity to the first and second electrodes for delivering therapeutic molecules to the tissue while the first and second electrodes generate the electric field to treat the tissue.

15. The catheter according to claim 14, wherein the second tubular member includes a handle coupled to a proximal portion thereof, the handle of the second tubular member disposed separate from the handle of the first tubular member when the second tubular member is in the second position.

16. The catheter according to claim 14, wherein the handle of the first tubular member includes a distal neck portion having a reduced diameter relative to a proximal portion of the handle of the first tubular member, the distal neck portion configured to be received within the access port of the bronchoscope to couple the handle of the first tubular member to the bronchoscope.

* * * * *